(12) United States Patent
Wonnacott

(10) Patent No.: US 11,890,217 B2
(45) Date of Patent: Feb. 6, 2024

(54) BRACES FOR IMMOBILIZING A CLAVICLE FRACTURE IN AN INFANT AND RELATED METHODS

(71) Applicant: Pediatric Answers, L.L.C., Highland, UT (US)

(72) Inventor: Monica C. Wonnacott, Highland, UT (US)

(73) Assignee: Pediatric Answers, L.L.C., Highland, UT (US)

( * ) Notice: Subject to any disclaimer, the term of this patent is extended or adjusted under 35 U.S.C. 154(b) by 646 days.

(21) Appl. No.: 16/948,626

(22) Filed: Sep. 25, 2020

(65) Prior Publication Data

US 2021/0085506 A1 Mar. 25, 2021

Related U.S. Application Data

(60) Provisional application No. 62/905,656, filed on Sep. 25, 2019.

(51) Int. Cl.
*A61F 5/058* (2006.01)
*A61F 5/37* (2006.01)
*A41D 13/12* (2006.01)

(52) U.S. Cl.
CPC ...... *A61F 5/05808* (2013.01); *A41D 13/1245* (2013.01); *A41D 13/1272* (2013.01); *A61F 5/05858* (2013.01); *A61F 5/3746* (2013.01); *A41D 2300/32* (2013.01); *A41D 2400/32* (2013.01)

(58) Field of Classification Search
CPC .............. A61F 5/05808; A61F 5/05858; A61F 5/3746; A41D 13/1245; A41D 13/1272; A41D 2300/32; A41D 2400/32
See application file for complete search history.

(56) References Cited

U.S. PATENT DOCUMENTS

| | | | |
|---|---|---|---|
| 3,780,729 A * | 12/1973 | Garnett | A61F 5/3738 602/4 |
| 3,857,388 A | 12/1974 | Frankel | |
| 4,198,964 A | 4/1980 | Honneffer et al. | |
| 4,480,637 A | 11/1984 | Florek | |
| 4,657,003 A | 4/1987 | Wirtz | |

(Continued)

FOREIGN PATENT DOCUMENTS

GB 2462727 A 2/2010

*Primary Examiner* — Tarla R Patel
(74) *Attorney, Agent, or Firm* — TraskBritt

(57) ABSTRACT

Braces for immobilizing clavicle fractures in infants may include a garment of fabric sized and shaped to extend around a torso and along at least one arm of an infant. The garment may include a first closure configured to secure the garment around the torso of the infant, a second closure configured to secure the garment over a shoulder corresponding to a fractured clavicle of the infant, and a sleeve configured to extend around an upper and lower arm of the infant on a same lateral side of the garment as the second closure. The sleeve may include at least a third closure configured to secure the sleeve around the upper and lower arm of the infant. A portion of the sleeve may be affixed to a portion of the garment, the portion of the garment to which the sleeve may be affixed being located over the torso of the infant when the garment is secured around the torso of the infant.

17 Claims, 13 Drawing Sheets

(56) References Cited

U.S. PATENT DOCUMENTS

| | | | | |
|---|---|---|---|---|
| 5,095,894 | A | * | 3/1992 | Marble ................ A61F 5/3746 |
| | | | | 602/62 |
| 8,277,402 | B2 | | 10/2012 | Chisena et al. |
| 10,376,404 | B2 | * | 8/2019 | Webster ................ A61F 5/0118 |
| 2012/0022417 | A1 | | 1/2012 | Thompson |
| 2017/0290696 | A1 | | 10/2017 | Quist |

* cited by examiner

BRACES FOR IMMOBILIZING A CLAVICLE FRACTURE IN AN INFANT AND RELATED METHODS

CROSS-REFERENCE TO RELATED APPLICATION

This application claims the benefit under 35 U.S.C. § 119(e) of U.S. Provisional Patent Application Ser. No. 62/905,656, filed Sep. 25, 2019, for BRACE FOR IMMOBILIZING A CLAVICLE FRACTURE IN AN INFANT AND RELATED METHODS, the disclosure of which is incorporated herein in its entirety by this reference.

FIELD

This disclosure relates generally to braces for immobilizing clavicle fractures in infants. More specifically, disclosed embodiments relate to braces that may better immobilize clavicle fractures in infants, speeding recovery and reducing adverse effects of clavicle fractures.

BACKGROUND

Clavicle fractures are fairly common injuries among infants as a result of childbirth. According to some reports, clavicle fractures are the most common among injuries to newborns sustained during childbirth and may occur in about 1 in every 50 births. Conventional treatments known to the inventor include securing a sleeve of the infant's regular clothing to the front of the regular clothing, such as by pinning the sleeve to the front of the clothing using a safety pin.

BRIEF SUMMARY

In some embodiments, braces for immobilizing clavicle fractures in infants may include a garment of fabric sized and shaped to extend around a torso and along at least one arm of an infant. The garment may include a first closure configured to secure the garment around the torso of the infant, a second closure configured to secure the garment over a shoulder corresponding to a fractured clavicle of the infant, and a sleeve configured to extend around an upper and lower arm of the infant on the same lateral side of the garment as the second closure. The sleeve may include at least a third closure configured to secure the sleeve around the upper and lower arm of the infant. A portion of the sleeve may be affixed to a portion of the garment, the portion of the garment to which the sleeve may be affixed being located over the torso of the infant when the garment is secured around the torso of the infant.

In other embodiments, methods of making braces for immobilizing clavicle fractures in infants may involve forming a garment of fabric sized and shaped to extend around a torso and along at least one arm of an infant. Forming the garment may involve positioning and configuring a first closure to secure the garment around the torso of the infant. A second closure may be positioned and configured to secure the garment over a shoulder corresponding to a fractured clavicle of the infant. A sleeve may be positioned and configured to extend around an upper and lower arm of the infant on a same lateral side of the garment as the second closure, the sleeve including at least a third closure configured to secure the sleeve around the upper and lower arm of the infant. A portion of the sleeve may be affixed to a portion of the garment, the portion of the garment to which the portion of the sleeve is affixed being located over the torso of the infant when the garment is secured around the torso of the infant.

In still other embodiments, methods of using braces to immobilize clavicle fractures in infants may involve surrounding a torso of an infant with a first portion of a garment and using a first closure to secure the first portion of the garment around the torso of the infant. A second portion of the garment may be secured over a shoulder corresponding to a fractured clavicle of the infant using a second closure. An upper and lower arm of an infant may be positioned in a sleeve on a same lateral side of the garment as the second closure, a portion of the sleeve being affixed to a portion of the garment, the portion of the garment to which the portion of the sleeve is affixed being located over the torso of the infant when the garment is secured around the torso of the infant. The sleeve may be secured around at least a portion of the upper and lower arm of the infant using at least a third closure.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

The illustrations presented in this disclosure are not meant to be actual views of any particular brace or component thereof, but are merely idealized representations employed to describe illustrative embodiments. Thus, the drawings are not necessarily to scale.

Disclosed embodiments relate generally to braces that may better immobilize clavicle fractures in infants, speeding recovery and reducing adverse effects of clavicle fractures. More specifically, disclosed are embodiments of braces for immobilizing clavicle fractures in infants that may include multiple closures and a sleeve sewn to a front region of a garment, better ensuring beneficial positioning of the infant's immobilized arm, more easily enabling the brace to be placed on the infant, and better ensuring that the infant is not able to move out of a desired positioning.

As used herein, the terms "substantially" and "about" in reference to a given parameter, property, or condition means and includes to a degree that one of ordinary skill in the art would understand that the given parameter, property, or condition is met with a degree of variance, such as within acceptable manufacturing tolerances. For example, a parameter that is substantially or about a specified value may be at least about 90% the specified value, at least about 95% the specified value, at least about 99% the specified value, or even at least about 99.9% the specified value.

Figure 1:
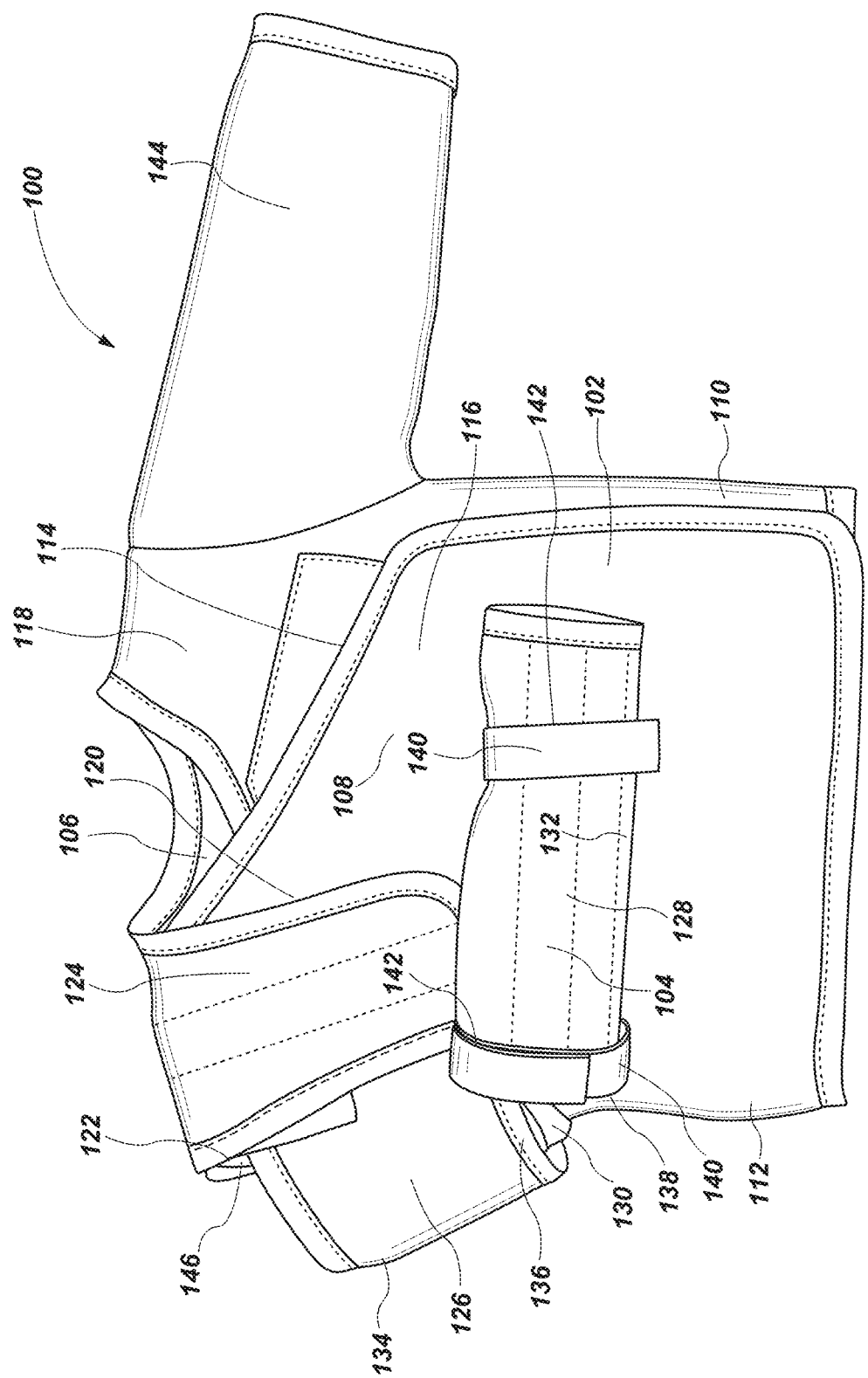
FIG. 1 is a front view of a brace in accordance with this disclosure.

FIG. 1 is a front view of a brace 100 in accordance with this disclosure. The brace 100 may be configured as, for example, a garment to be worn by the infant. More specifically, the brace 100 may include a torso portion 102 and a sleeve 104. The torso portion 102 may include, for example, one or more panels of fabric sized, shaped, and sewn together (where more than one panel is employed) to be located around at least a portion of a torso of an infant. More specifically, the torso portion 102 may include a back region 106 sized, shaped, and positioned to be located over and cover at least a portion of the infant's back when the brace 100 is worn by the infant. The torso portion 102 may further include a front region 108 sized, shaped, and positioned to be located over and cover at least a portion of the infant's chest and belly when the brace 100 is worn by the infant. The torso portion 102 may also include a left lateral side region 110 and a right lateral side region 112, which may be sized, shaped, and positioned to be located over and cover at least a portion of the infant's respective left and right lateral sides underneath the armpit when the brace 100 is worn by the infant. As a specific, nonlimiting example, the back region 106 of the torso portion 102 may be sized, shaped, and positioned to be located over and cover the infant's back from the nape of the neck to the lower back when the brace 100 is worn by the infant. The left lateral side region 110 and the right lateral side region 112 of torso portion 102 may extend laterally from the back region 106, around the flanks of the infant's torso underneath the armpits, to the front region 108.

A maximum height of the torso portion, as measured from a location of the back region 106 to be located at or near the nape of the neck to a location of the back region to be located at or near the lower back or buttocks when the brace 100 is worn by the infant, may be, for example, less than about 12 inches. More specifically, the maximum height of the torso portion 102 may be, for example, between about 7 inches and about 11 inches. As a specific, nonlimiting example, the maximum height of the torso portion 102 may be between about 8 inches and about 10 inches (e.g., about 9 inches). The front region 108 of the torso portion 102 may be sized, shaped, and positioned to be located over and cover the infant's chest and belly from proximate to the neck to below the belly button when the brace 100 is worn by the infant.

The torso portion 102 may include a first closure 114 configured to secure the garment around the torso of the infant. For example, the first closure 114 may include laterally overlapping sections of one or more of the front region 108, back region 106, left lateral side region 110, and right lateral side region 112 and may extend longitudinally from an upper portion of the garment to a lower portion of the garment. More specifically, the first closure 114 may include a first laterally overlapping section 116 extending from one of the left lateral side region 110 or the right lateral side region 112 toward the other of the left lateral side region 110 or right lateral side region 112 at the front region 108, forming an opening extending longitudinally from proximate to the infant's neck to proximate the infant's waist when the brace 100 is worn by the infant. As a specific, nonlimiting example, the first closure 114 may include one of the hooks or loops of a hook-and-loop closure on a backside of one of the first laterally overlapping section 116 or the second laterally overlapping section 118 of the front region 108 and the other of the hooks or loops of a hook-and-loop closure on a front side of the other of the first laterally overlapping section 116 or second laterally overlapping section 118 of the front region 108. Such a first closure 114 may enable the garment to be opened to easily place an infant thereon, easily secure the torso portion 102 around the torso of the infant, and adjust a circumference of the torso portion 102 of the garment to better fit a given infant.

A maximum circumference of the torso portion 102 formable using the first closure 114 may be, for example, about 28 inches or less. For example, the actual maximum circumference of the torso portion 102 when the first closure 114 is in the closed state may be between about 12 inches and about 26 inches. More specifically, the actual maximum circumference of the torso portion 102 when the first closure 114 is in the closed state may be, for example, between about 14 inches and about 24 inches. As a specific, nonlimiting example, the actual maximum circumference of the torso portion 102 when the first closure 114 is in the closed state may be between about 16 inches and about 22 inches (e.g., about 18 inches or 20 inches).

The torso portion 102 may include a second closure 120 configured to secure the garment over a shoulder corresponding a fractured clavicle of the infant. For example, the second closure 120 may include longitudinally overlapping sections of the front region 108 and the back region 106 and may extend from the back region 106, over the shoulder of the infant, to the front region 108. More specifically, the second closure 120 may include a first shoulder flap 122 extending from the front region 108, over the infant's right or left shoulder, toward the back region 106, and a second shoulder flap 124 extending from the back region 106, over the same right or left shoulder, toward the front region 108, such that the first shoulder flap 122 and the second shoulder flap 124 overlap with one another. As a specific, nonlimiting example, the second closure 120 may include one of the hooks or loops of a hook-and-loop closure on a backside of one of the first shoulder flap 122 or the second shoulder flap 124 and the other of the hooks or loops of a hook-and-loop closure on a front side of the other of the first shoulder flap 122 or the second shoulder flap 124. Such a second closure 120 may enable the garment to be opened to easily place an infant thereon and reduce the likelihood that the act of securing the garment over a shoulder of the infant will aggravate or displace the fractured clavicle.

The sleeve 104 of the brace 100 may be sized, shaped, positioned, and configured to extend around at least a portion of an upper and lower arm of the infant on a same lateral side of the garment as the second closure 120. For example, the sleeve 104 may include an upper arm section 126 sized, shaped, positioned, and configured to at least partially surround the upper arm of the infant at least from just below the infant's shoulder and armpit proximate to the fractured clavicle at least to just above the infant's inner and outer elbow. The sleeve 104 may also include a lower arm section 128 sized, shaped, positioned, and configured to at least partially surround the lower arm of the infant at least from just below the infant's elbow on the lateral side of the infant where the fractured clavicle is located toward the infant's hand. More specifically, the upper arm section 126 of the sleeve 104 may completely surround the upper arm of the infant from just below the infant's shoulder and armpit proximate to the fractured clavicle to just above the infant's inner and outer elbow when the brace 100 is worn by the infant. The lower arm section 128 of the sleeve 104 may completely surround the lower arm of the infant from just below the infant's elbow on the lateral side of the infant where the fractured clavicle is located to just above the infant's hand (e.g., around the infant's wrist) when the brace 100 is worn by the infant.

In some embodiments, the sleeve 104 may include an elbow opening 130 located between the upper arm section 126 and the lower arm section 128. For example, the upper arm section 126 may include a lower boundary 136 extending at least partially around a circumference of the sleeve 104 proximate to the infant's elbow, and the lower arm section 128 may include an upper boundary 138 extending at least partially around the circumference of the sleeve 104 proximate to the infant's elbow. The elbow opening 130 may include the space defined between the lower boundary 136 of the upper arm section 126 and the upper boundary 138 of the lower arm section 128. More specifically, the elbow opening 130 may expose at least a portion of the inner elbow of the infant, and optionally at least a portion of the outer elbow of the infant, when the brace 100 is worn by the infant.

In some embodiments, the sleeve 104 may include a shoulder opening 146 located between the upper arm section 126 and the second closure 120. For example, the shoulder opening 146 may include the space defined between an uppermost extent of the upper arm section 126 and a laterally outermost extent of the second closure 120. More specifically, the shoulder opening 146 may expose at least a portion of the shoulder of the infant when the brace 100 is worn by the infant.

A maximum length of the sleeve 104, as measured from a portion of the upper arm section 126 proximate to the second closure 120 to a distal end of the lower arm section 128 to be located at or proximate the infant's hand when the brace 100 is worn by the infant, may be, for example, about 18 inches or less. More specifically, the maximum length of the sleeve 104 may be, for example, between about 12 inches and about 17 inches. As a specific, nonlimiting example, the maximum length of the sleeve 104 may be between about 14 inches and about 16 inches (e.g., about 15 inches).

The sleeve 104 may include at least a third closure 134 configured to secure the sleeve 104 around the upper and lower arm of the infant. For example, the third closure 134 may extend along at least a portion of the sleeve 104 and enable the sleeve 104 to be opened for positioning of at least a portion of the infant's arm therein and closed for securing the portion of the infant's arm in the sleeve 104. More specifically, the sleeve 104 may include laterally overlapping sections of the upper arm section 126 and may extend longitudinally from an upper extent to a lower extent of the upper arm section 126. As a specific, nonlimiting example, the third closure 134 may include one of the hooks or loops of a hook-and-loop closure on a backside of one of the laterally overlapping sections of the upper arm section 126 and the other of the hooks or loops of a hook-and-loop closure on a front side of the other of the laterally overlapping sections of the upper arm section 126. Such a third closure 134 may enable the upper arm section 126 to be opened to easily place at least the upper arm of an infant therein, easily secure at least the upper arm section 126 around the upper arm of the infant, and adjust a circumference of at least the upper arm section 126 of the garment to better immobilize the arm of a given infant.

In embodiments where the third closure 134 is located only within the upper arm section 126 of the sleeve 104, the sleeve 104 may include a fourth closure 132 configured to secure the sleeve 104 around the lower arm of the infant. For example, the fourth closure 132 may include longitudinally overlapping sections of the lower arm section 128 and may extend laterally from a first lateral extent to a second, opposite lateral extent of the lower arm section 128. As a specific, nonlimiting example, the fourth closure 132 may include one of the hooks or loops of a hook-and-loop closure on a backside of one of the longitudinally overlapping sections of the lower arm section 128 and the other of the hooks or loops of a hook-and-loop closure on a front side of the other of the longitudinally overlapping sections of the lower arm section 128. Such a fourth closure 132 may enable the lower arm section 128 to be opened to easily place the lower arm of an infant therein, easily secure the lower arm section 128 around the lower arm of the infant, and adjust a circumference of the lower arm section 128 of the garment to better immobilize the arm of a given infant.

A maximum circumference of the sleeve 104 formable using the third closure 134 and/or the fourth closure 132 may be, for example, about 8 inches or less. For example, the actual average circumference of the sleeve 104 when the third closure 134 and the fourth closure 132 are in the closed state may be between about 2.5 inches and about 7.5 inches. More specifically, the actual maximum circumference of the sleeve 104 when the third closure 134 and the fourth closure 132 are in the closed state may be, for example, between about 3 inches and about 7 inches. As a specific, nonlimiting example, the actual maximum circumference of the sleeve 104 when the third closure 134 and the fourth closure 132 are in the closed state may be between about 4 inches and about 6 inches (e.g., about 5 inches).

At least a portion of the sleeve 104 may be affixed to a portion of the garment, the portion of the garment to which some portion of the sleeve 104 is affixed being located over the torso of the infant when the garment is secured around the torso of the infant. For example, at least the lower arm section 128 of the sleeve 104 may be affixed to the front region 108 of the torso portion 102 of the garment. More specifically, the lower arm section 128 may be sewn to the front region 108 of the torso portion 102 utilizing one or more regions of stitching extending laterally from proximate to the upper arm section 126 toward an opposite lateral side of the front region 108. As a specific, nonlimiting example, the lower arm section 128 may be sewn to the front region 108 utilizing one or more seams (e.g., a single seam, two seams at upper and lower locations on the lower arm section 128) from proximate to one of the left lateral side region 110 or the right lateral side region 112 toward the other of the left lateral side region 110 or the right lateral side region 112. Such a fixed positioning for at least the lower arm section 128 of the sleeve 104 may enable the brace 100 to better immobilize the arm of an infant in a position adapted to hasten healing of a fractured clavicle and/or reduce the size of the callus formed during the process of healing a fractured clavicle.

Another portion of the sleeve 104 may be affixed to one of the left lateral side region 110 or the right lateral side region 112. For example, at least the upper arm section 126 of the sleeve 104 may be affixed to one of the left lateral side region 110 or the right lateral side region 112 of the garment. More specifically, the upper arm section 126 may be sewn to one of the left lateral side region 110 or the right lateral side region 112 utilizing one or more regions of stitching extending longitudinally along at least a portion of the upper arm section 126. As a specific, nonlimiting example, the upper arm section 126 may be sewn to one of the left lateral side region 110 or the right lateral side region 112 utilizing one or more seams (e.g., a single seam, two seams) from proximate to the armpit of the infant toward the belly of the infant when the brace 100 is worn by the infant.

In some embodiments, the brace 100 may include at least one support strap 140 positioned and configured to further secure one or more portions of the sleeve 104 in place. For example, each support strap 140 may extend circumferentially around one of the upper arm section 126 or the lower arm section 128 of the sleeve 104, and may be configured to open and close around the upper arm section 126 or the lower arm section 128. More specifically, each support strap 140 may extend circumferentially around the lower arm section 128 of the sleeve 104, and may include one of the hooks or loops of a hook-and-loop closure on a backside of one portion of the support strap 140 and the other of the hooks or loops of a hook-and-loop closure on a front side of another portion of the support strap 140. As a specific, nonlimiting example, each support strap 140 may be sewn to the front region 108 of the torso portion 102 of the garment at its ends and may include a fifth closure 142 enabling the support strap 140 to open and close around the lower arm section 128 of the sleeve 104. Such a support strap 140 may better enable the garment to support and immobilize the infant's arm during healing of the fractured clavicle and may reduce the likelihood that the infant may be able to undesirably move its arm or remove its arm from the sleeve 104. In other embodiments, the support straps 140 may be omitted, and the brace 100 may rely solely on any seams 202 (see FIG. 2) between the lower arm section 128 and the front region 108, as well as the fourth closure 132, to support and immobilize the lower arm of an infant during healing of a fractured clavicle.

In some embodiments, the brace 100 may further include another sleeve 144 located on a contralateral side of the garment opposite the sleeve 104 for supporting the arm of the infant correlating to the fractured clavicle. For example, the other sleeve 144 may include a tube of fabric sized shaped and positioned to receive an arm of the infant therein on a contralateral side of the infant's body opposite the fractured clavicle. More specifically, the torso portion 102 of the garment may extend over the infant's shoulder on a contralateral side of the garment opposite the second closure 120, and the other sleeve 144 may extend from the torso portion 102 proximate to the infant's shoulder away from the torso portion 102 to proximate the infant's hand when the brace 100 is worn by the infant. As a specific, nonlimiting example, the other sleeve 144 may be located on one of the left lateral side region 110 or the right lateral side region 112 proximate to an uppermost portion of the garment, and the sleeve 104 may be located on the other of the left lateral side region 110 or the right lateral side region 112 proximate to the uppermost portion of the garment.

Although FIG. 1 depicts the brace 100 as having the sleeve 104 configured to support the arm of the infant corresponding to the fractured clavicle and the second closure 120 on the right lateral side region 112 and the other sleeve 144 on the left lateral side region 110, braces 100 in accordance with this disclosure are not so limited. For example, the sleeve 104 configured to support the arm of the infant corresponding to the fractured clavicle and the second closure 120 may be located on the left lateral side region 110 and the other sleeve 144 may be located on the right lateral side region 112. As a result, different braces 100 in accordance with this disclosure may be adapted to address a clavicle fracture in an infant located on the left or right side of the infant's body.

The fabric of at least the torso portion 102, first shoulder flap 122, second shoulder flap 124, and sleeve 104 may include or be formed from a non-stretch fabric. For example, the fabric of the brace 100 may be free of elastic materials. More specifically, the fabric of the brace 100 may be free of elastomeric polymer materials. Forming the brace 100, or at least portions thereof, from a stiff, non-stretch fabric, may better enable the brace 100 to better support the arm of the infant corresponding to the fractured clavicle and reduce the likelihood that the infant may be able to move it's arm from the desired placement or remove the sleeve 104 and/or brace 100.

Figure 2:
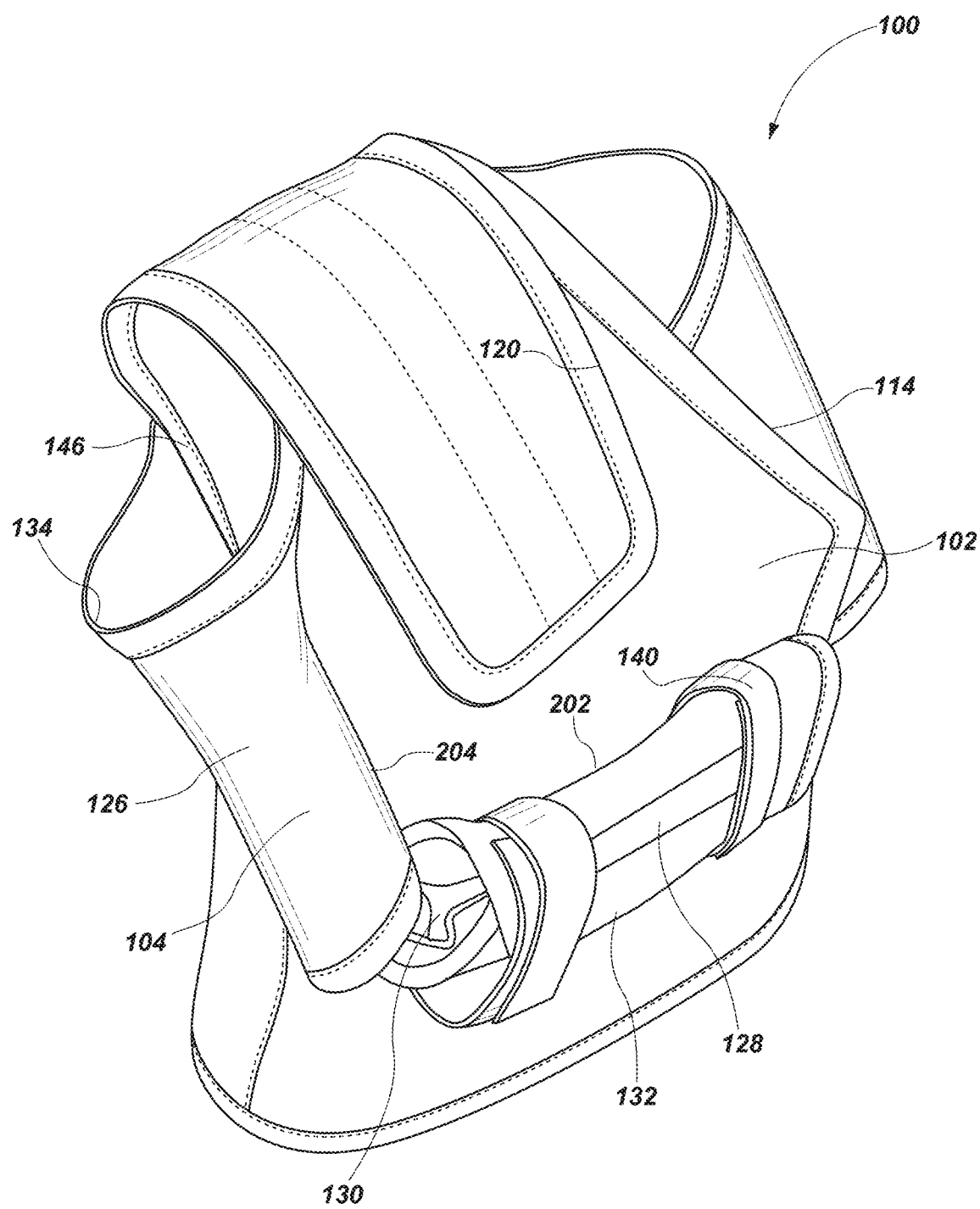
FIG. 2 is a perspective side view of the brace of FIG. 1.

FIG. 2 is a perspective side view of the brace 100 of FIG. 1. The lower arm section 128 may be sewn to the front region 108 utilizing one or more first seams 202 extending along the lower arm section 128 from proximate to one of the left lateral side region 110 or the right lateral side region 112 toward the other of the left lateral side region 110 and the right lateral side region 112. For example, the lower arm section 128 may be sewn to the front region 108 utilizing a single first seam 202 extending from one of a left- or right-side lateral extent of the lower arm section 128 to the other of the left- or right-side lateral extent of the lower arm section 128, the first seam 202 being located circumferentially central on the lower arm section 128 relative to an average center of an overlap between the longitudinally overlapping sections of the lower arm section 128 forming the fourth closure 132.

The upper arm section 126 may be sewn to one of the left lateral side region 110 or the right lateral side region 112 utilizing one or more second seams 204 extending along the lower arm section 128 from proximate to the shoulder opening 146 toward the elbow opening 130. For example, the upper arm section 126 may be sewn to the front region 108 utilizing two second seams 204 extending around a portion of a periphery of the shoulder opening 146 and converging with one another into a single second seam 204 extending along one of the left lateral side region 110 or the right lateral side region 112 to the elbow opening 130. The portion of the second seam 204 extending along one of the left lateral side region 110 or the right lateral side region 112 may be located circumferentially central on the upper arm section 126 relative to an average center of an overlap between the laterally overlapping sections of the upper arm section 126 forming the third closure 134.

Figure 3:
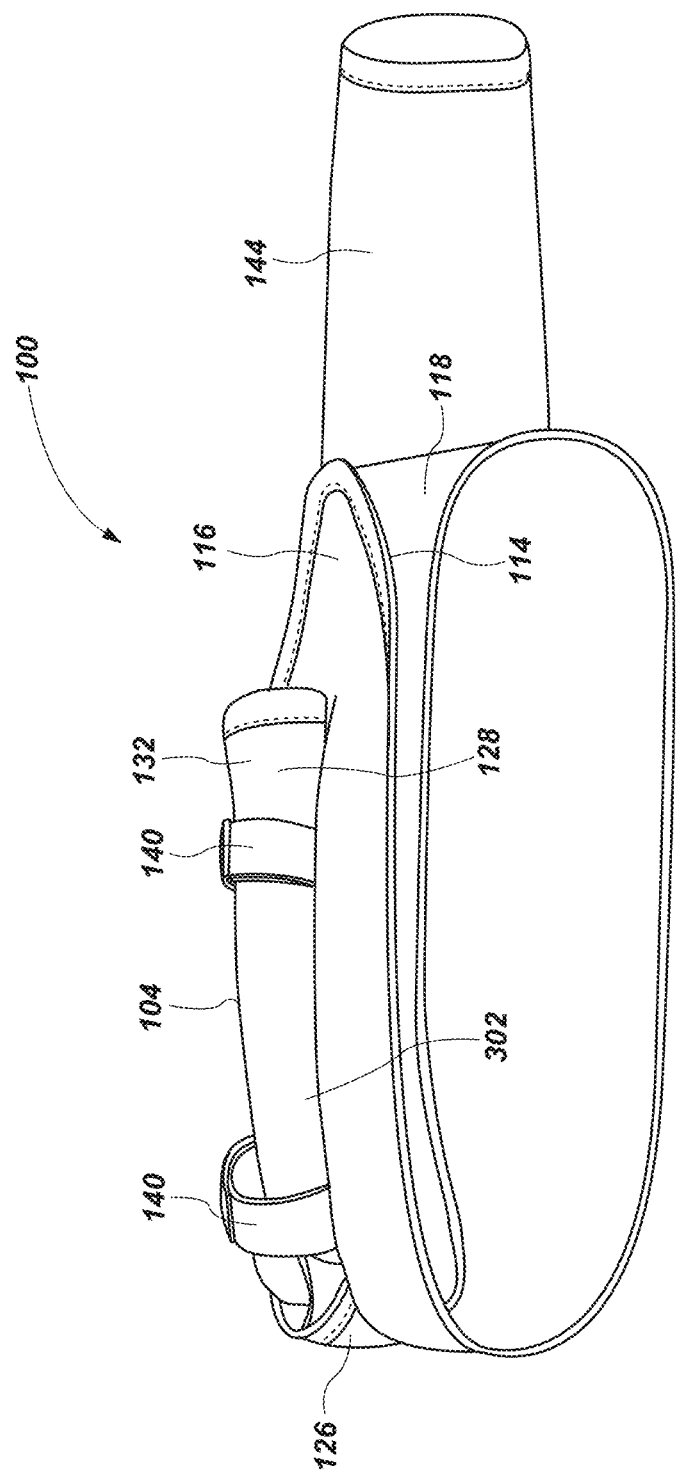
FIG. 3 is a bottom view of the brace of FIG. 1.

FIG. 3 is a bottom view of the brace 100 of FIG. 1. In some embodiments, the brace 100 may include a reinforcement material 302 extending along at least a portion of the sleeve 104. For example, the reinforcement material 302 may be positioned to extend along a laterally distal portion of the upper arm section 126 of the sleeve 104 and along the ulna of the infant when the sleeve 104 of the brace 100 is secured around the arm of the infant. More specifically, the reinforcement material 302 may be sewn into at least a portion of the sleeve 104 and may extend along the outer portion of the arm of the infant continuously from the upper arm at the upper extent of the upper arm section 126 to the lower arm at the lateral extent of the lower arm section 128.

The reinforcement material 302 may be configured as, for example, a strip or rod positionable into a seam or pocket along the sleeve 104. The reinforcement material 302 may include a material having a higher stiffness than the stiffness of the fabric material of the garment. For example, the reinforcement material 302 may include a plastic, metal, or metal alloy material.

Figure 4:
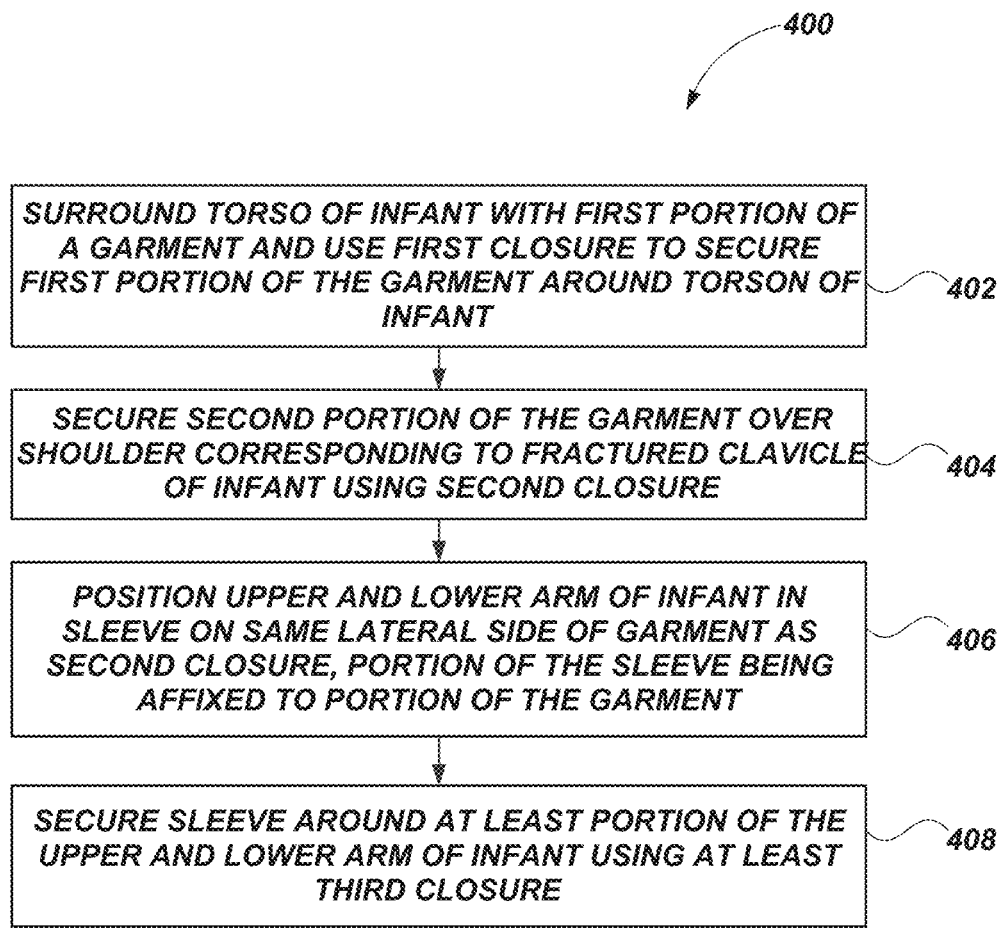
FIG. 4 is a flowchart of a method of using the brace of FIG. 1 to immobilize a clavicle of an infant.
Figure 5:
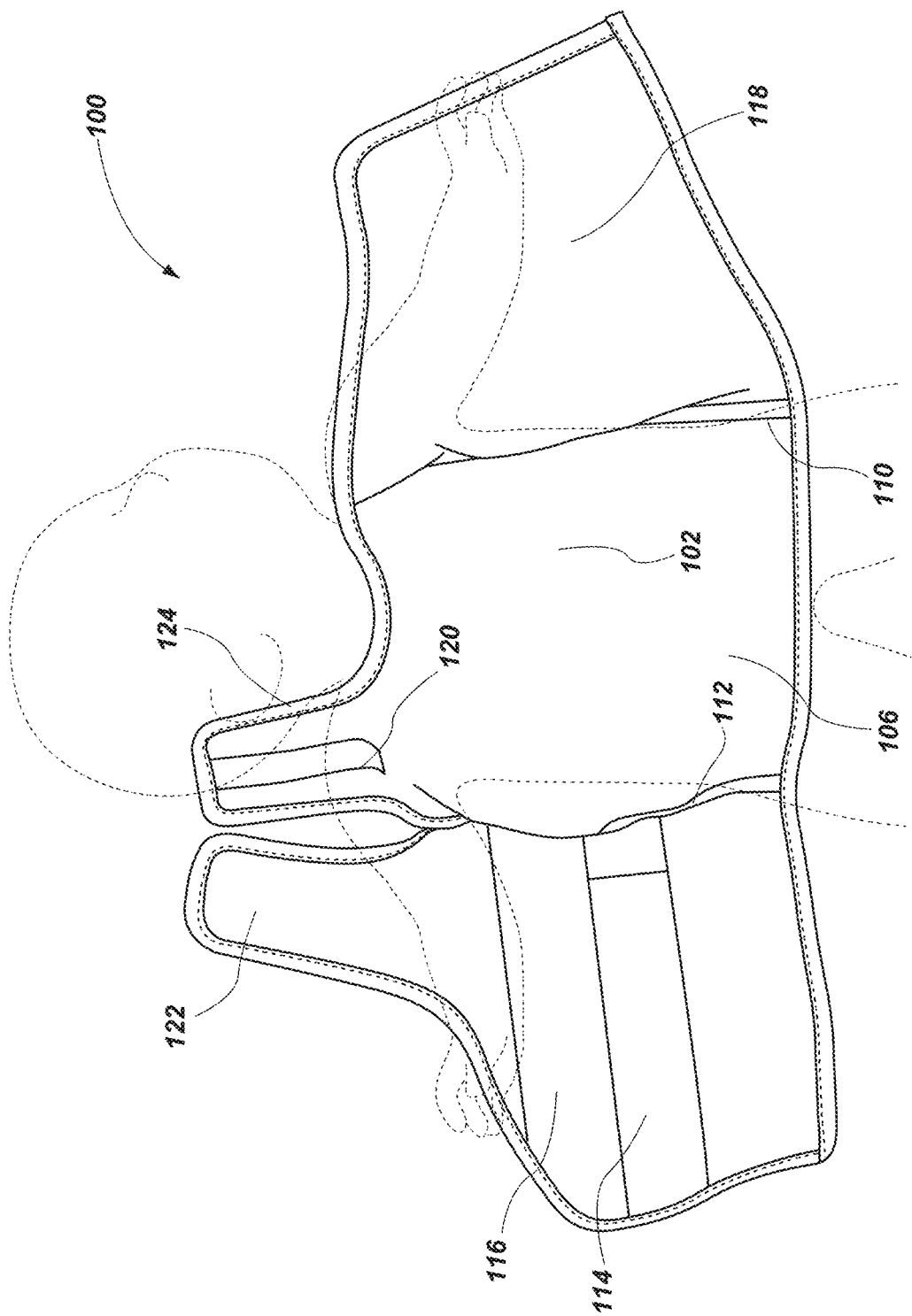
FIG. 5 is a front view of the brace of FIG. 1 during a first stage of using the brace to immobilize a clavicle of an infant.
Figure 6:
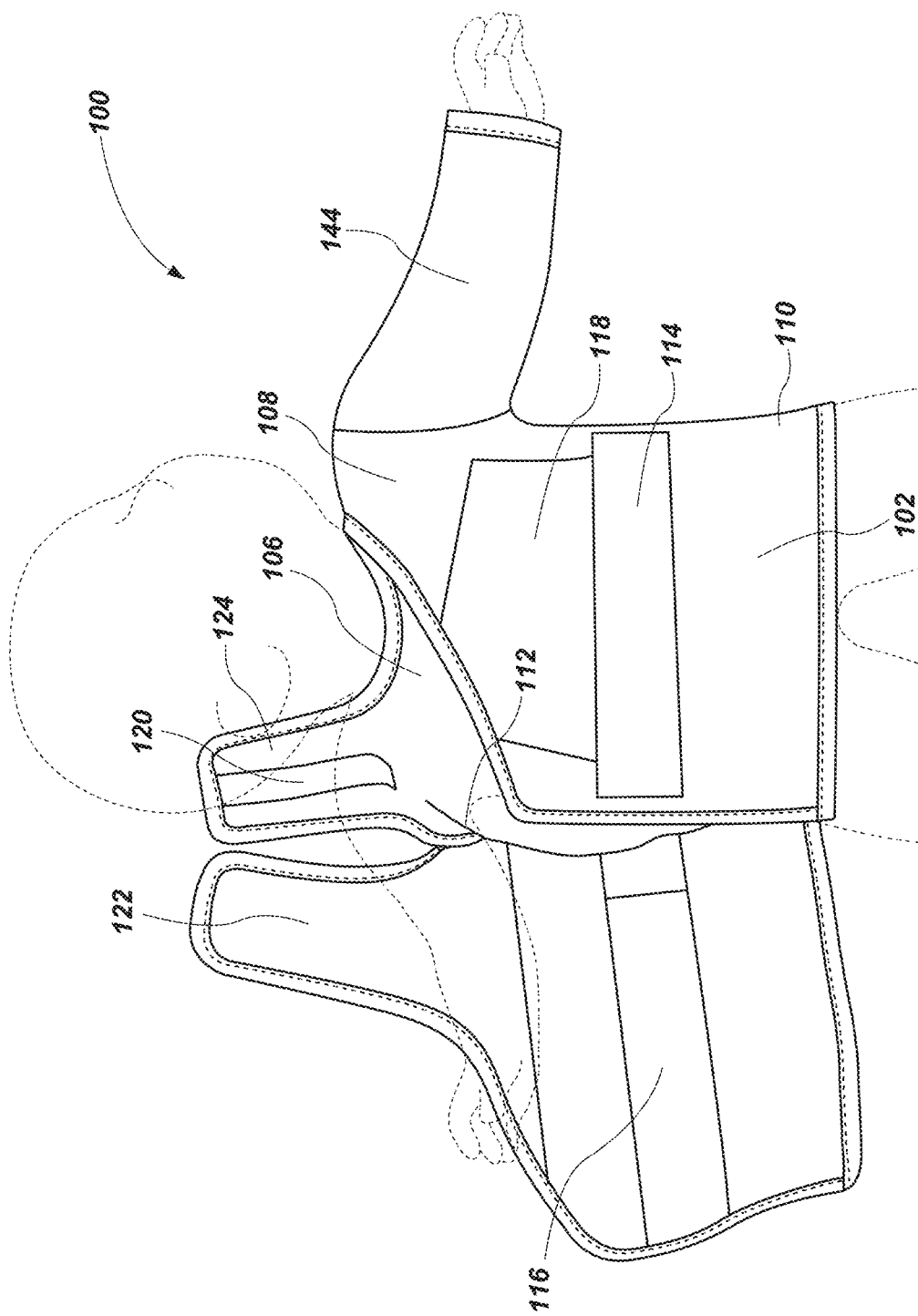
FIG. 6 is a front view of the brace of FIG. 1 during a second stage of using the brace to immobilize a clavicle of an infant.
Figure 7:
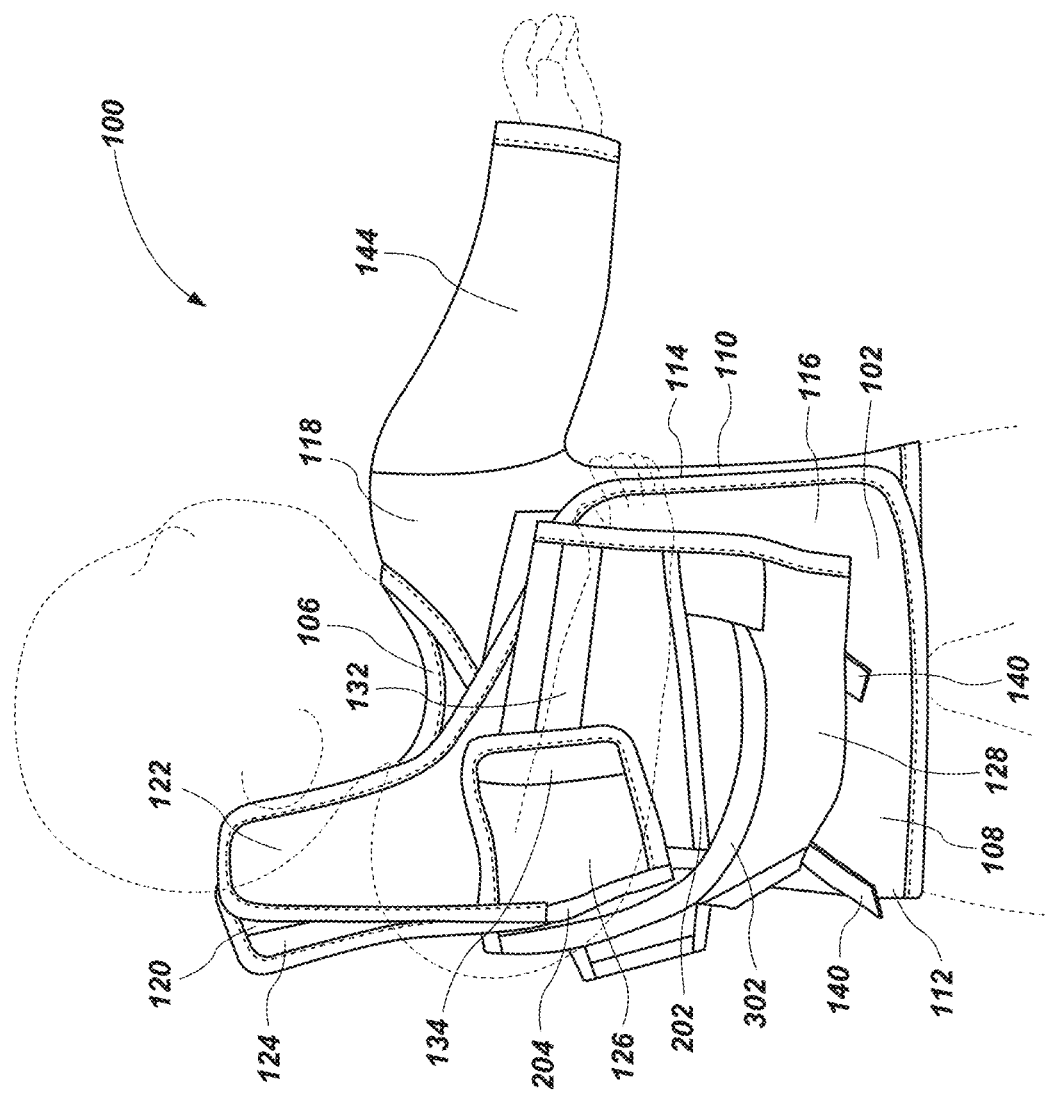
FIG. 7 is a front view of the brace of FIG. 1 during a third stage of using the brace to immobilize a clavicle of an infant.

FIG. 4 is a flowchart of a method 400 of using the brace 100 of FIG. 1 to immobilize a clavicle of an infant. FIG. 5 is a front view of the brace 100 of FIG. 1 during a first stage of using the brace 100 to immobilize a clavicle of an infant. FIG. 6 is a front view of the brace 100 of FIG. 1 during a second stage of using the brace 100 to immobilize a clavicle of an infant. FIG. 7 is a front view of the brace 100 of FIG. 1 during a third stage of using the brace 100 to immobilize a clavicle of an infant. With combined reference to FIGS. 4 through 7, the method 400 may involve surrounding a torso of an infant with a first portion of a garment and using a first closure 114 to secure the portion of the garment around the torso of the infant, as shown at block 402. For example, as a precursor to performing the act of block 402, each of the first closure 114, second closure 120, third closure 134, and fourth closure 132 and each support strap 140 may be opened, placing the brace 100 into a first, fully opened state corresponding to the first stage of FIG. 5. The infant may be placed on the torso portion 102 of the brace 100, and the arm of the infant opposite the fractured clavicle may be inserted into the other sleeve 144. The infant's torso may be generally centered over the torso portion 102, and the back region 106 the torso portion 102 may be located underneath the infant's back and may generally extend from proximate the nape of the infant's neck to, and at least partially covering, the infant's lower back.

Once the infant has been placed on the torso portion 102, and the infant's arm on a lateral side of the infant opposite the fractured clavicle has been inserted into the other sleeve 144, the second laterally overlapping section 118 may be moved laterally to cover at least a portion of the chest and belly of the infant. For example, the second laterally overlapping section 118 may be moved from the right lateral side region 112 toward the left lateral side region 110 or from the left lateral side region 110 toward the right lateral side region 112, placing the brace 100 into a second state, as shown in FIG. 6. The first laterally overlapping section 116 may then be moved laterally to cover at least a portion of the chest and belly of the infant. For example, the first laterally overlapping section 116 may be moved from the right lateral side region 112 toward the left lateral side region 110 or from the left lateral side region 110 toward the right lateral side region 112, whichever is opposite to the movement for the second laterally overlapping section 118. The first closure 114 may then be closed to secure the torso portion 102 around the torso of the infant, placing the brace 100 into a third state, as shown in FIG. 7. For example, the extent to which the first laterally overlapping section 116 is moved laterally may be tailored to secure the torso portion 102 snugly around the infant's torso once the first closure 114 is placed in a closed state.

Figure 8:
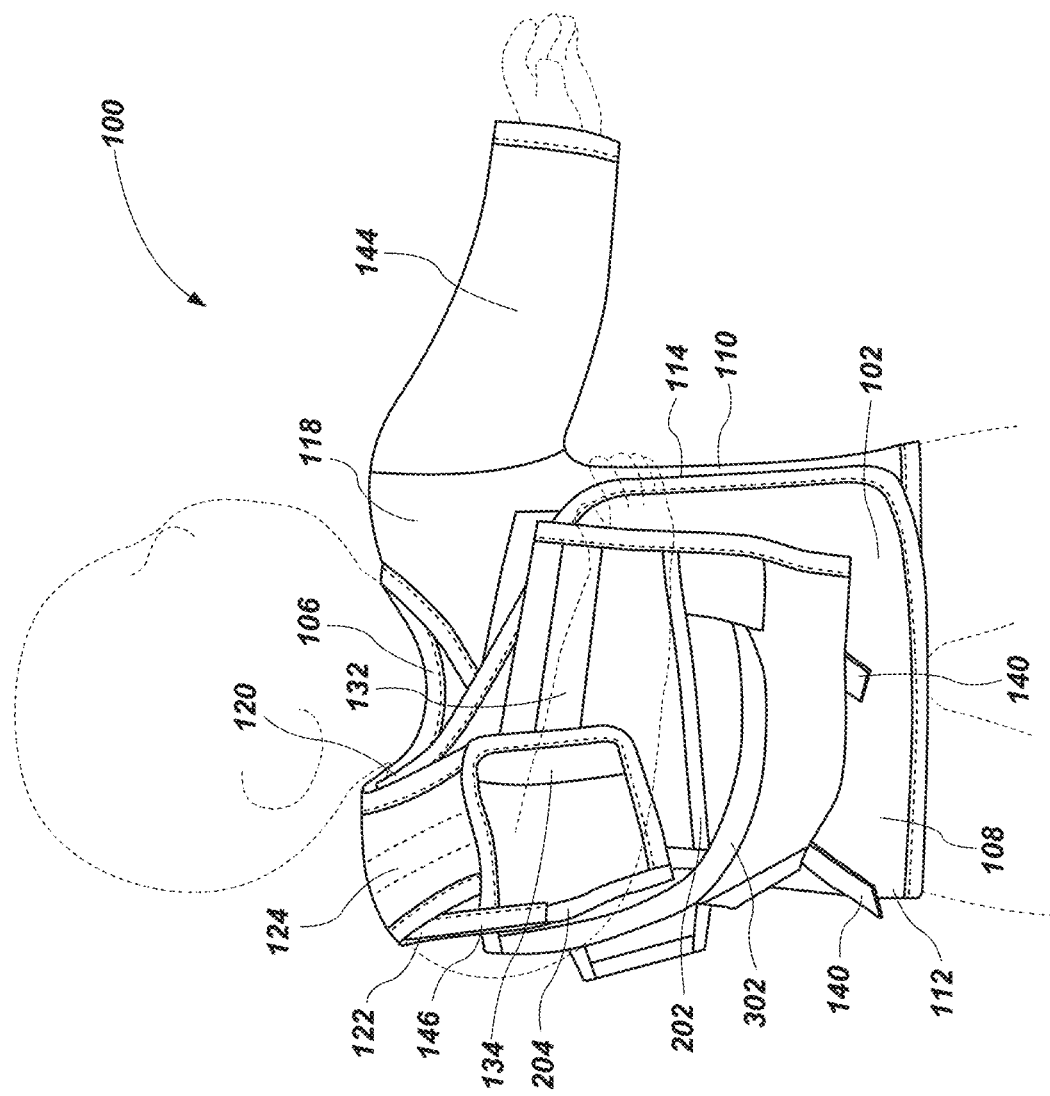
FIG. 8 is a front view of the brace of FIG. 1 during a fourth stage of using the brace to immobilize a clavicle of an infant.

FIG. 8 is a front view of the brace 100 of FIG. 1 during a fourth stage of using the brace 100 to immobilize a clavicle of an infant. With combined reference to FIGS. 4, 7, and 8, the method 400 may involve securing a second portion of the garment over a shoulder corresponding to a fractured clavicle of the infant using a second closure 120, as shown in block 404. For example, the first shoulder flap 122 may be tucked behind the shoulder of the infant corresponding to the fractured clavicle between the infant's back and the back region 106 of the torso portion 102 of the brace 100. The second shoulder flap 124 may be brought over the first shoulder flap 122 and down toward the chest of the infant, leaving the infant's arm corresponding to the fractured clavicle extending out through the shoulder opening 146. The second closure 120 may then be closed to further secure the torso portion 102 in place on the torso of the infant, placing the brace 100 into a fourth state, as shown in FIG. 8.

Figure 9:
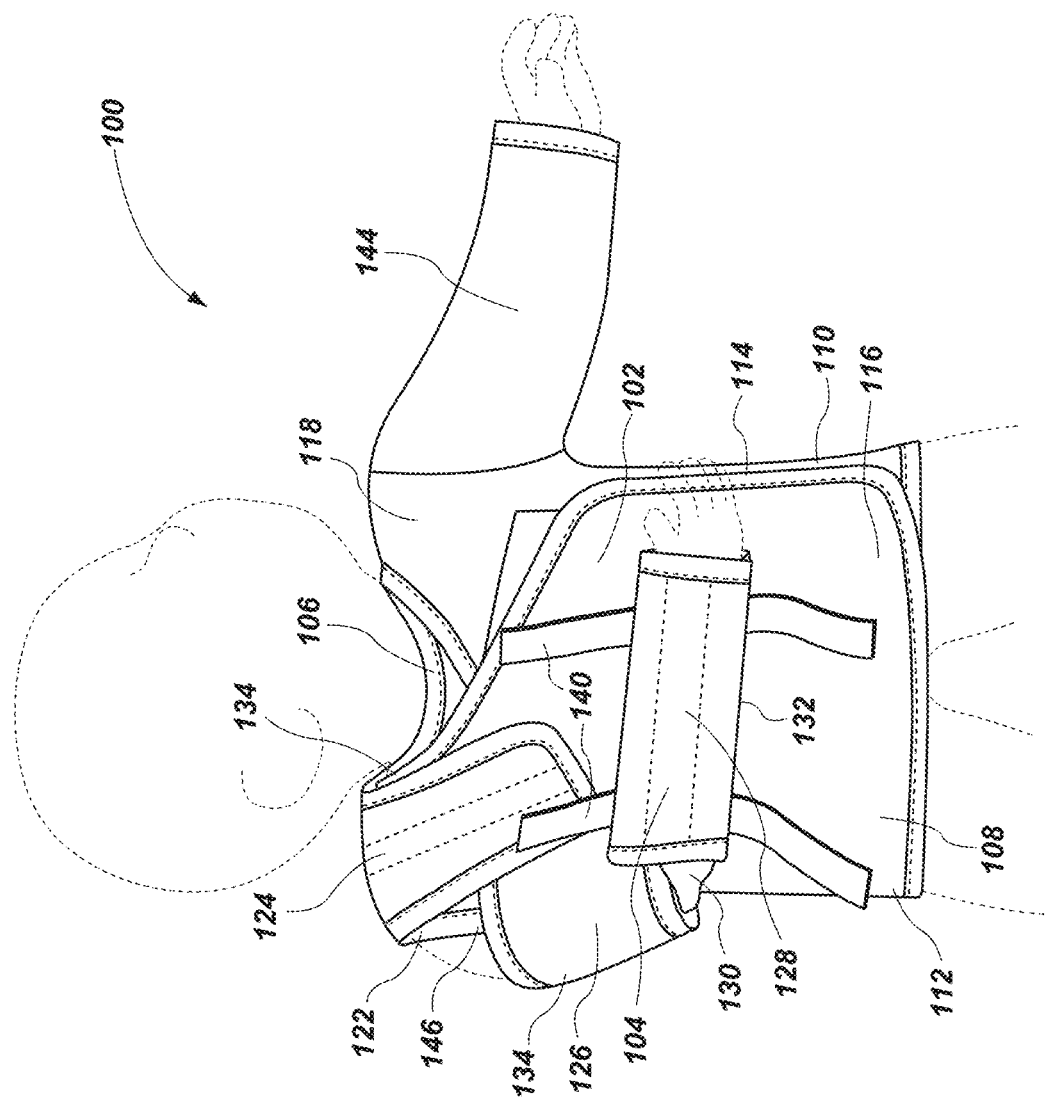
FIG. 9 is a front view of the brace of FIG. 1 during a fifth stage of using the brace to immobilize a clavicle of an infant.

FIG. 9 is a front view of the brace 100 of FIG. 1 during a fifth stage of using the brace 100 to immobilize a clavicle of an infant. With combined reference to FIGS. 4, 8, and 9, the method 400 may further involve positioning an upper and lower arm of an infant in the sleeve 104 on a same lateral side of the garment as the second closure 120, as indicated at block 406. The sleeve may then be secured around at least a portion of the upper and lower arm of the infant using at least a third closure 134, as indicated at block 408. For example, the upper arm of the infant may be placed within the upper arm section 126, and the third closure 134 may be placed in a closed state snugly around the infant's upper arm to secure the infant's upper arm within the upper arm section 126. The lower arm of the infant may be placed within the lower arm section 128, and the fourth closure 132 may be placed in a closed state snugly around the infant's lower arm to secure the infant's lower arm within the lower arm section 128, placing the brace 100 into a fifth state, as shown in FIG. 9. Finally, each support strap 140 may be wrapped around an associated portion of the sleeve 104 and placed into a closed state around the associated portion of the sleeve 104 to further secure the infant's arm in place. For example, each support strap 140 may be wrapped around an associated portion of the lower arm section 128 and secured around the lower arm section 128, as shown in FIG. 1.

Figure 10:
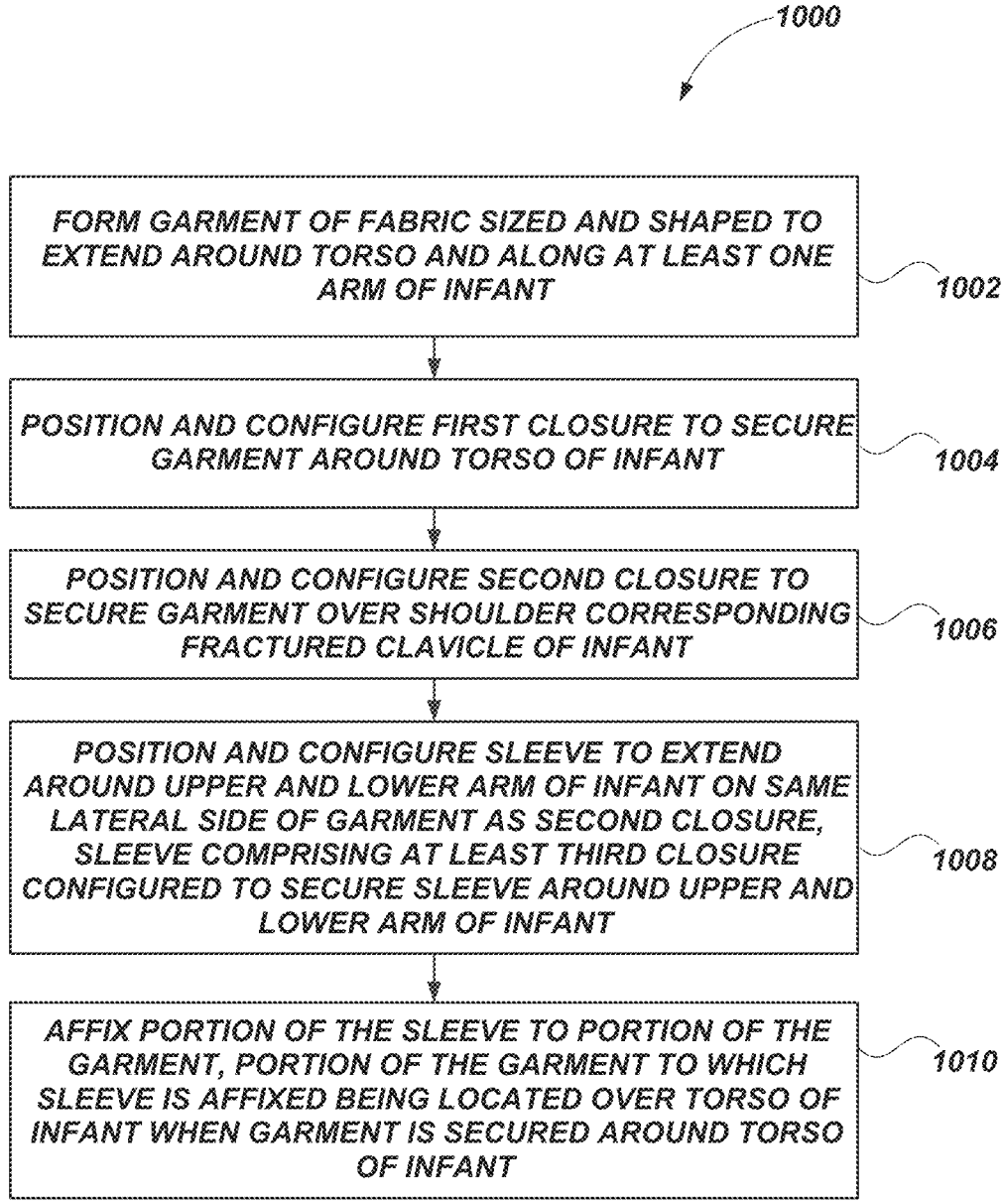
FIG. 10 is a flowchart of a method of making the brace of FIG. 1.

FIG. 10 is a flowchart of a method 1000 of making the brace 100 of FIG. 1. The method 1000 may involve forming a garment of fabric sized and shaped to extend around a torso and along at least one arm of an infant, as indicated at block 1002. Forming the garment may involve, for example, positioning and configuring a first closure 114 to secure the garment around the torso of the infant, as indicated at block 1004. For example, the garment may be provided with a torso portion 102 having a first laterally overlapping section 116 and a second laterally overlapping section 118 with the first closure 114 therebetween. A second closure 120 may be positioned and configured to secure the garment over a shoulder corresponding to a fractured clavicle of the infant, as indicated at block 1006. For example, the torso portion 102 of the garment may be provided with a first shoulder flap 122 extending from a front region 108 of the torso portion 102 and a second shoulder flap 124 extending from a back region 106 of the torso portion 102, the first shoulder flap 122 and the second shoulder flap 124 being configured to overlap with, and be secured to, one another to form the second closure 120. A sleeve 104 may be positioned and configured to extend around an upper and lower arm of the infant on a same lateral side of the garment as the second closure 120, as indicated at block 1008. For example, the sleeve 104 may include an upper arm section 126 having a third closure 134 and a lower arm section 128 having a fourth closure 132 for receiving and securing the infant's upper and lower arm within the respective section 126 or 128 of the sleeve 104. Finally, method 1000 may involve affixing a portion of the sleeve 104 to a portion of the garment, the portion of the garment to which the portion of the sleeve 104 is affixed being located over the torso of the infant when the garment is secured around the torso of the infant, as indicated at block 1010. For example, at least the lower arm section 128 of the sleeve 104 may be sewn to a front region 108 of the torso portion 102 of the garment, such that the lower arm section 128 may be oriented laterally across the torso portion 102.

Figure 11:
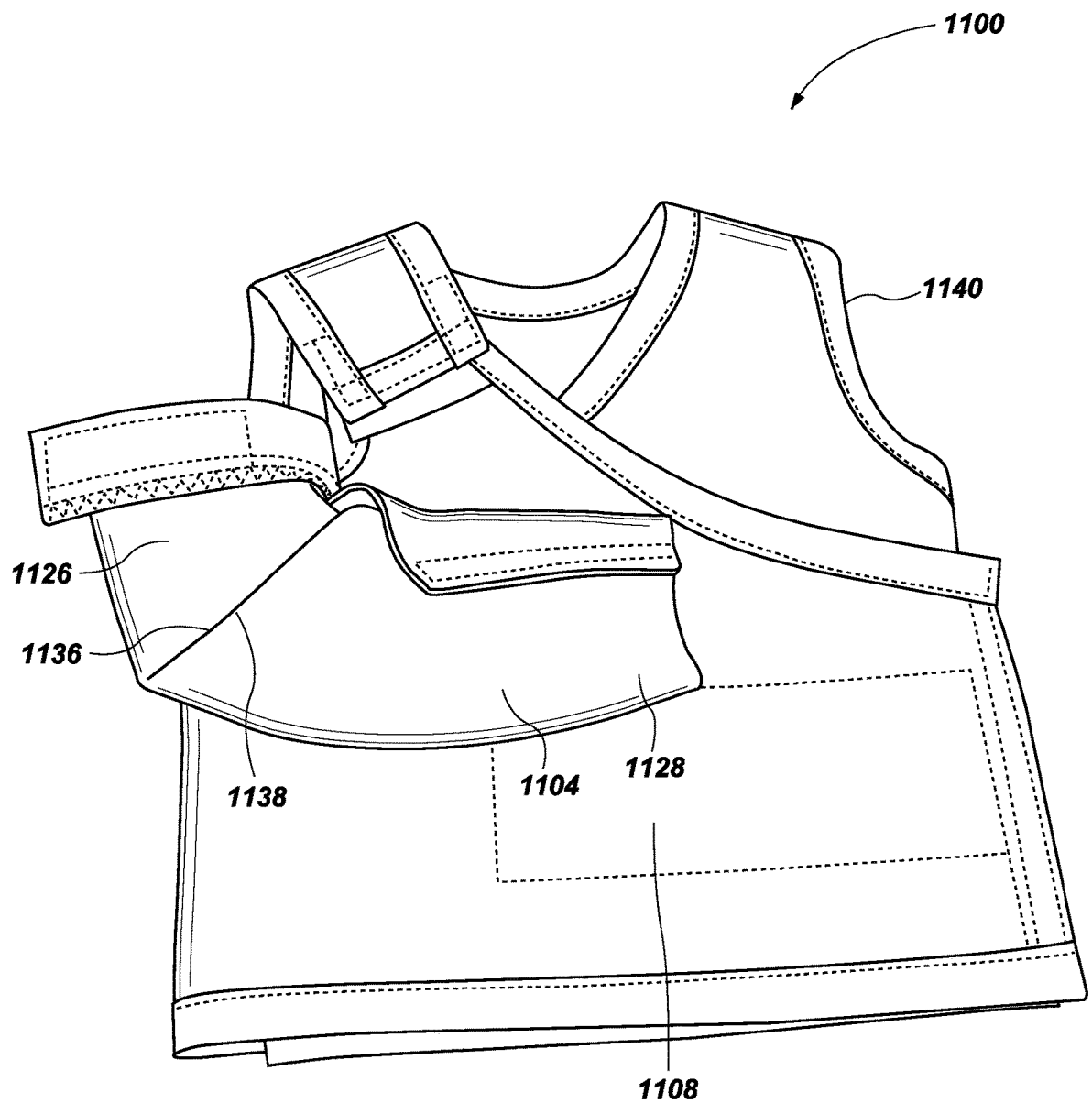
FIG. 11 is a front view of another embodiment of a brace in accordance with this disclosure.
Figure 12:
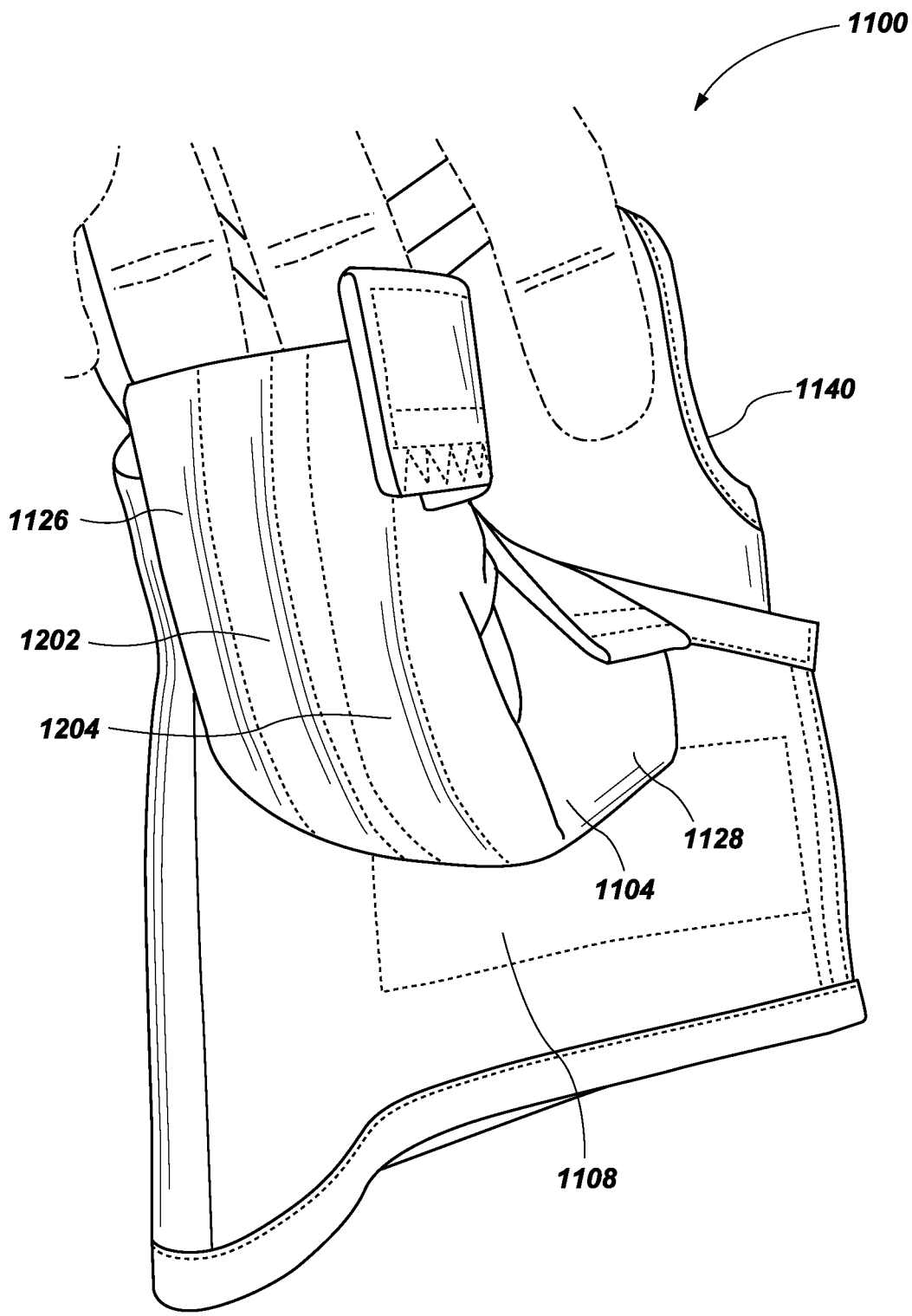
FIG. 12 is a perspective side view of the brace of FIG. 11.
Figure 13:
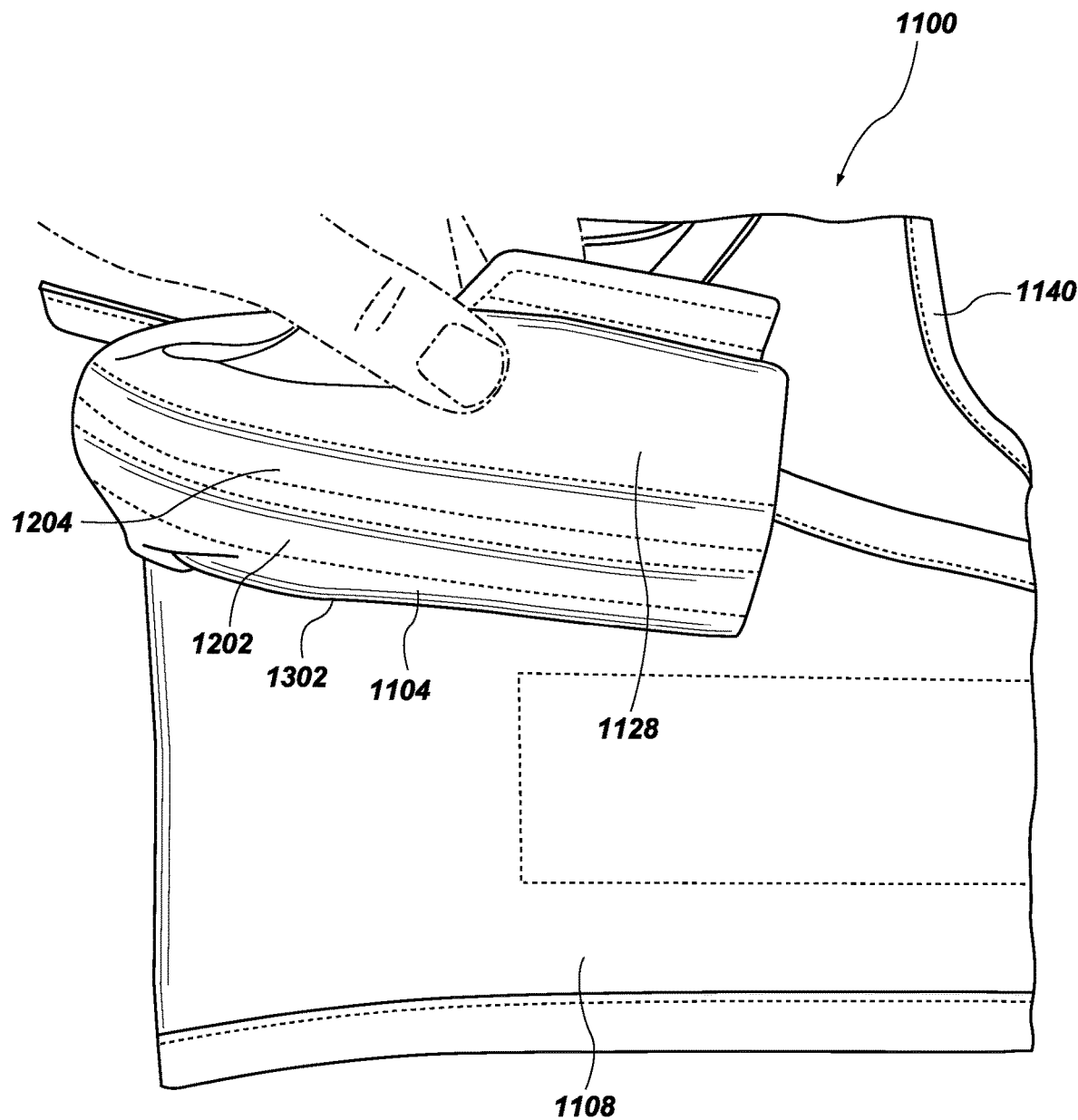
FIG. 13 is a front view of the brace of FIG. 11, with a lower arm section of a sleeve of the brace lifted so as to reveal certain features thereof.

FIG. 11 is a front view of another embodiment of a brace 1100 in accordance with this disclosure. FIG. 12 is a perspective side view of the brace 1100 of FIG. 11. FIG. 13 is a front view of the brace 1100 of FIG. 11, with a lower arm section 1128 of a sleeve 1104 of the brace 1100 lifted so as to reveal certain features thereof. The brace 1100 of FIGS. 11 through 13 may be at least substantially similar to the brace 100 of FIGS. 1 through 3 and 5 through 9, with certain variations in the design of the brace 1100 highlighted below. In addition, similar features have been numbered in a manner corresponding to the numbering in FIGS. 1 through 3 and 5 through 9 for the sake of consistency.

With collective reference to FIGS. 11 through 13, the brace 1100 may include two quantities of reinforcement material to increase the support for the arm. For example, and as best shown in FIGS. 12 and 13, the brace 1100 may include a first reinforcement material 1202 extending along the sleeve 1104 from the upper arm section 1126, along the inner arm of the infant, to a distal portion of the lower arm section 1128. More specifically, the first reinforcement material 1202 may include, for example, a strip, rod, wire, or other elongated mass of semi-rigid material (e.g., plastic, metal, metal alloy) located within a pouch, pocket, or seam extending from an upper portion of the upper arm section 1126, contiguously along the sleeve 1104, to a distal portion of the lower arm section 1128. Continuing the example, the second reinforcement material 1204 may include a strip, rod, wire, or other elongated mass of semi-rigid material (e.g., plastic, metal, metal alloy) located within a pouch, pocket, or seam circumferentially offset from the pouch, pocket, or seam in which the first reinforcement material 1202 is located, and extending from an upper portion of the upper arm section 1126, contiguously along the sleeve 1104, to a distal portion of the lower arm section 1128.

The first reinforcement material 1202, the second reinforcement material 1204, or both may be located between the arm of the infant and the belly of the infant, or below the arm of the infant, when the brace 1100 is worn by the infant and the arm of the infant is secured within the sleeve 1104. The first reinforcement material 1202 and the second reinforcement material 1204 may be located closer to the waist of the infant than the seam 1302 securing the lower arm section 1128 to the front portion 1108 of the brace 1100 when the sleeve 1104 is open to receive the arm of the infant therein, like the orientation and state of application shown in FIG. 7. Providing two reinforcement materials may enable elimination of the support straps 140 (see FIG. 1), enabling easier, simpler placement on an infant without jeopardizing the support provided to the arm during healing.

In some embodiments, the brace 1100 may lack the elbow opening 130 (see FIG. 1) between the upper arm section 1126 and the lower arm section 1128 of the sleeve 1104. For example, the lower boundary 1136 of the upper arm section 1126 may be joined with the upper boundary 1138 of the lower arm section 1128 at a seam, forming a contiguous enclosure to surround the arm of an infant. Closing the elbow opening 130 (see FIG. 1) at a seam between the upper arm section 1126 and the lower arm section 1128 may reduce the likelihood that an infant may force its lower arm out of the lower arm section 1128 and out of the brace 1100 through the elbow opening 130 (see FIG. 1). In still other embodiments, the upper arm section and the lower arm section may be formed from one contiguous sheet of fabric, lacking any seam or opening therebetween.

In some embodiments, and as best shown in FIG. 11, the brace 1100 may lack any sleeve 144 (see FIG. 1) located on a lateral side of the brace 1100 opposite the sleeve 1104 for supporting the arm of the infant correlating to the fractured clavicle. For example, the brace 1100 may include a sleeveless opening 1140 through which the arm of an infant lacking any clavicle fracture may extend. Such a configuration may reduce the quantity of fabric required to produce the brace 1100 without compromising on support for the arm having the clavicle fracture, and may enable use of the brace 1100 in a greater variety of situations (e.g., when heat may render wearing a sleeve uncomfortable for the infant).

Braces in accordance with this disclosure may better address problems associated with treating fractured clavicles in infants when compared to known techniques for immobilizing clavicle fractures. For example, braces in accordance with this disclosure may enable easier positioning onto an infant, ensure more beneficial placement and immobilization of the fractured clavicle and associated arm, and reduce the likelihood that the infant will be able to displace the associated arm relative to the desired positioning. More specifically, the provision of multiple closures for the torso portion and sleeve of the brace, as well as the affixation of portions of the sleeve to the torso portion, may better suit the braces in accordance with this disclosure to treatment of clavicle fractures, particularly within infants.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may be made to produce embodiments within the scope of this disclosure, such as those specifically claimed, including legal equivalents. In addition, features from one disclosed embodiment may be combined with features of another disclosed embodiment while still being within the scope of this disclosure, as contemplated by the inventor.

What is claimed is:

1. A brace for immobilizing a clavicle fracture in an infant, comprising:
 a garment of fabric sized and shaped to extend around a torso and along at least one arm of an infant, the garment comprising:
 a first closure configured to secure the garment around the torso of the infant;
 a second closure configured to secure the garment over a shoulder corresponding a fractured clavicle of the infant;
 a sleeve configured to extend around an upper and lower arm of the infant on a same lateral side of the garment as the second closure, the sleeve comprising at least a third closure configured to secure the sleeve around the upper and lower arm of the infant; and a reinforcement material extending along at least a portion of the sleeve, wherein the reinforcement material is positioned to extend along a laterally distal portion of the upper arm and along the ulna of the infant when the sleeve of the brace is secured around the arm of the infant;
 wherein a portion of the sleeve is affixed to a portion of the garment, the portion of the garment to which the portion of the sleeve is affixed being located over the torso of the infant when the garment is secured around the torso of the infant.

2. The brace of claim 1, wherein the reinforcement material comprises a plastic, metal, or metal alloy material.

3. The brace of claim 1, wherein the reinforcement material is sewn into the at least a portion of the sleeve.

4. The brace of claim 1, further comprising at least one support strap positioned and configured to extend around a portion of the lower arm of the infant and around the sleeve.

5. The brace of claim 4, wherein the at least one support strap is affixed to the portion of the garment located over the torso of the infant when the garment is secured around the torso of the infant.

6. The brace of claim 1, wherein the portion of the sleeve is sewn to the portion of the garment located over the torso of the infant when the garment is secured around the torso of the infant.

7. The brace of claim 1, wherein the at least a third closure of the sleeve extends along at least a portion of the upper arm and the lower arm of the infant when the sleeve surrounds the upper and the lower arm of the infant.

8. The brace of claim 1, wherein the sleeve comprises a first portion positioned to surround at least a portion of the upper arm of the infant and comprising the at least a third closure and a second portion positioned to surround at least a portion of the lower arm of the infant and comprising a fourth closure.

9. The brace of claim 8, wherein the portion of the sleeve affixed to the portion of the garment is the second portion of the sleeve and wherein the first portion is affixed to another portion of the garment on a lateral side of the garment.

10. The brace of claim 1, wherein the fabric is free of elastic materials.

11. The brace of claim 1, wherein the fabric is a non-stretch fabric.

12. The brace of claim 1, wherein each of the first closure, the second closure, and the at least a third closure comprises a hook-and-loop closure.

13. The brace of claim 1, further comprising another sleeve located on a lateral side of the garment opposite the sleeve.

14. The brace of claim 1, wherein the first closure is further configured to adjust a circumference of the portion of the garment configured to extend around the torso of the infant.

15. A method of making a brace for immobilizing a clavicle fracture in an infant, comprising:
  forming a garment of fabric sized and shaped to extend around a torso and along at least one arm of an infant, wherein forming the garment comprises:
  positioning and configuring a first closure to secure the garment around the torso of the infant;
  positioning and configuring a second closure to secure the garment over a shoulder corresponding to a fractured clavicle of the infant;
  positioning and configuring a sleeve to extend around an upper and lower arm of the infant on a same lateral side of the garment as the second closure, the sleeve comprising at least a third closure configured to secure the sleeve around the upper and lower arm of the infant affixing a reinforcement material along at least a portion of the sleeve and to extend along a laterally distal portion of the upper arm and along the ulna of the infant when the sleeve of the brace is secured around the arm of the infant; and
  affixing a portion of the sleeve to a portion of the garment, the portion of the garment to which the portion of the sleeve is affixed being located over the torso of the infant when the garment is secured around the torso of the infant.

16. A method of using a brace to immobilize a clavicle fracture in an infant, comprising:
  surrounding a torso of an infant with a first portion of a garment of fabric and using a first closure to secure the first portion of the garment around the torso of the infant;
  securing a second portion of the garment over a shoulder corresponding to a fractured clavicle of the infant using a second closure;
  positioning an upper and lower arm of an infant in a sleeve on a same lateral side of the garment as the second closure, a portion of the sleeve being affixed to a portion of the garment, the portion of the garment to which the portion of the sleeve is affixed being located over the torso of the infant when the garment is secured around the torso of the infant; wherein positioning the upper and lower arm of the infant in the sleeve comprises positioning the upper and lower arm of the infant proximate to a reinforcement material extending along at least a portion of the sleeve, wherein the reinforcement material extending along a laterally distal portion of the upper arm and along the ulna of the infant when the sleeve of the brace is secured around the arm of the infant; and
  securing the sleeve around at least a portion of the upper and lower arm of the infant using at least a third closure.

17. The method of claim 16, further comprising securing at least one support strap around a portion of the sleeve located around a portion of the lower arm of the infant after securing the sleeve around the at least a portion of the upper and lower arm of the infant.

* * * * *